United States Patent [19]

Basava et al.

[11] Patent Number: 5,364,840
[45] Date of Patent: * Nov. 15, 1994

[54] SYNTHETIC CALCITONIN PEPTIDES

[75] Inventors: Channa Basava, San Diego; Karl Y. Hostetler, Del Mar, both of Calif.

[73] Assignee: Vical, Inc., San Diego, Calif.

[*] Notice: The portion of the term of this patent subsequent to Dec. 29, 2009 has been disclaimed.

[21] Appl. No.: 711,180

[22] Filed: Jun. 5, 1991

Related U.S. Application Data

[63] Continuation-in-part of Ser. No. 572,674, Aug. 24, 1990, Pat. No. 5,175,146, which is a continuation-in-part of Ser. No. 446,932, Dec. 6, 1989, abandoned.

[51] Int. Cl.$^5$ .................... A61K 37/00; A61K 37/02; A61K 37/30; C07K 5/00
[52] U.S. Cl. .................... 514/12; 530/307; 530/324
[58] Field of Search ................ 530/307, 324; 514/12

[56] References Cited

U.S. PATENT DOCUMENTS

| | | |
|---|---|---|
| 3,849,388 | 11/1974 | Rittel et al. |
| 3,910,872 | 10/1975 | Riniker et al. .......... 530/324 |
| 4,397,780 | 8/1983 | Orlowski et al. |
| 4,401,593 | 8/1983 | Orlowski et al. |
| 4,537,716 | 8/1985 | Orlowski et al. |
| 4,597,900 | 7/1986 | Orlowski et al. |
| 4,606,856 | 8/1986 | Seyler et al. |
| 4,613,500 | 9/1986 | Suzuki et al. |
| 4,622,386 | 11/1986 | Orlowski et al. |
| 4,639,510 | 1/1987 | Orlowski et al. |
| 4,659,804 | 4/1987 | Orlowski et al. |
| 4,663,309 | 5/1987 | Kaiser et al. .......... 514/11 |
| 4,692,422 | 9/1987 | Hostetler et al. |
| 4,758,550 | 7/1988 | Cardinaux et al. |

FOREIGN PATENT DOCUMENTS

| | | |
|---|---|---|
| 0297159 | 7/1987 | European Pat. Off. |
| 8909786 | 4/1989 | European Pat. Off. |
| 8703884 | 7/1987 | France |
| 9012809 | 11/1990 | WIPO |
| 9107978 | 6/1991 | WIPO |

OTHER PUBLICATIONS

Gennari, C., et al., "Calcitonin in Bone Pain Management" Current Therapeutic Resch 44(5):712–722 (1988).

Breimer, L., et al., "Peptides from the Calcitonin Genes; molecular genetics, structure and function" Biochem J. 255:377–390 (1988).

Marx, et al., "Calcitonin Receptors of Kidney and Bone" Science 178:998–1001 (1972).

Epand, R. et al., "Conformational Flexibility and Biological Activity of Salmon Calcitonin" Biochemistry 25:1964–1968 (1988).

Habener, J. et al., "Explanation for Unusual Potency of Salmon Calcitonin" Nature (London) 232:91–92 (1971).

Kaiser, E. T., et al., "Amphiphilic Secondary Structure: Design of Peptide Hormones" Science 223:249–255 (1984).

Blaug, S. Remington's Pharmaceutical Sciences, 15th Ed. Mack Publishing Co., Easton, Pa. 18042 (1975).

Barany, G., et al., The Peptides, vol. 2; E. Gross & J. Meienhoffer, eds.; Academic Press, New York, pp. 3–284 (1979).

Pietta, P. et al., "Amide Protection and Amide Supports in Solid-Phase Peptide Synthesis" J. Chem. Soc. D, 650–651 (1970).

Channabasavaiah, K. et al., "New Analogues of Lulib- (List continued on next page.)

Primary Examiner—Lester L. Lee
Assistant Examiner—A. M. Davenport
Attorney, Agent, or Firm—Knobbe, Martens, Olson & Bear

[57] ABSTRACT

Synthetic hypocalcemic peptides which are superior in biological properties to native calcitonins as clinically useful agents. The peptides comprise analogues of native calcitonins having amino acid additions at the N-terminal position which, either alone or together with substitutions, and deletions at other residues, act to improve potency, prolong duration of the hormonal effect, and increase oral or nasal bioavailability. Methods are provided for the synthesis of these peptides.

16 Claims, No Drawings

OTHER PUBLICATIONS erin Which Inhibit Ovulation in the Rat" Biochem. Biophys. Res. Commun., 86, 1266–1273, (1979).

Kaiser, E. et al., "Color Test for Determination of Free Terminal Amino Groups in the Solid–Phase Synthesis of Peptides" Anal. Biochem. 34, 595–8, (1969).

Gennari, C. "Rationale for the Analgesic Effect of Calcitonin in Bone Pain Management" (Abstract) Calcitonin: State of the Art in Bone Metabolism, Atlanta, Ga., Aug. 27, 1990.

Kumar, M. et al., "A Biological Assay for Calcitonin" J. Endocrin. 33:469–475 (1965).

Lasmoles F., et al., "Elucidation of the Nucleotide Sequence of Chicken Calcitonin mRNA: Direct Evidence for the Expression of a Lower Vertebrate Calcitonin--like Gene in Man and Rat", The EMBO Journal 4(10):2603–2607 (1985).

Liedtke, R., et al., "Centrifugal Analysis with Automated Sequential Reagent Addition: Measurement of Serum Calcium" Clin. Chem. 27(12):2025–2028 (1981).

SYNTHETIC CALCITONIN PEPTIDES

SYNTHETIC CALCITONIN PEPTIDES

This application is a continuation-in-part of application Ser. No. 07/572,674, filed Aug. 24, 1990, now U.S. Pat. No. 5,175,146 and which is a continuation-in-part of application Ser. No 07/446,932, filed Dec. 6, 1989, and now abandoned which are hereby expressly incorporated by reference.

BACKGROUND OF THE INVENTION

This invention relates to synthetic peptides having hypocalcemic activity similar to that of natural caicitonins of various species. It relates specifically to synthetic calcitonin peptides having a hypocalcemic potency when administered to humans greater than that of human calcitonin and/or having less immunogenicity in humans than calcitonins from foreign species. It relates as well to synthetic procedures for producing these synthetic peptides.

Calcitonins are 32-amino acid peptide hormones involved in the regulation of calcium metabolism. Calcitonin participates with parathyroid hormone in the regulation of bone metabolism and the homeostatic regulation of blood calcium levels according to mechanisms that are not completely understood. Normal bone metabolism comprises a balance of osteolytic resorption and osteoblastic formation of new bone to fill the resorption spaces. Calcitonin appears to oppose the osteolytic activity of parathyroid hormone, acting directly to inhibit bone resoration by altering osteoclastic and osteocytic activity. Caicitonin may also enhance new bone formation by stimulation of osteoblasts.

Calcitonin has a normalizing effect on serum calcium levels. In the normal individual, bone resorption is minimal and exogenous calcitonin has no hypocalcemic effect. However, in some pathological conditions, unopposed bone resorption causes a release of calcium and alkaline phosphatase into the circulation, and the appearance of urinary hydroxyproline, resulting from the breakdown of collagen-containing bone matrix. According to physiological mechanisms, elevated serum calcium levels promote the secretion of calcitonin to exert a hypocalcemic effect.

In addition to inhibiting the destruction of bone, accelerating the formation of new bone and controlling calcemia, calcitonin reduces calciuria and fixes calcium within the cell. Calcitonin also has important analgesic properties.

Exogenous calcitonin is therapeutically useful in disorders wherein bone turnover or resorption is accelerated. One important disease of this type is osteoporosis, particularly the postmenopausal type, marked by a progressive loss of bone mass. The efficacy of calcitonin treatment in osteoporosis is determined by increased total body calcium. Another disease of this type is Paget's disease (osteitis deformans), a disorder characterized by excessive resorption of bone accompanied by the imbalanced formation of new (pagetic) bone which lacks the characteristic architecture of normal bone. Effective calcitonin treatment reduces the elevated serum levels of alkaline phosphatase and urinary hydroxyproline seen in individuals with this diserase. Benefits of calcitonin therapy in Paget's disease are indicated by radiologic evidence of bone remodeling, correlated with a reduced number of osteoclasts seen in bone biopsies, consistent with a decrease in bone resorption.

Calcitonin therapy is useful in treating hypercalcemia, a condition that can be life-threatening if it persights. Hypercalcemia occurs with primary hyperthyroidism and in malignant diseases, principally carcinoma and malignant myeloma. The condition can occur when tumors are metastatic to bone as well as in carcinoma without metastasis.

Calcitonin also provides relief from the bone pain that accompanies bone resorption as in Paget's disease, osteoporosis, osteolysis of malignancy, and osteoporotic vertebral fractures. Calcitonin pain relief activity appears to be distinct from the effect exerted by the hormone on bone. When calcitonin therapy is employed, for example, in the treatment of Paget's disease, the analgesic effect precedes any change in the biochemical markers of bone disease, and pain relief persists even in patients who experience renewed episodes of bone lesions (Gennari, C. and D. Agnusdei, *Current Therapeutic Research* 44(5):712-722 (1988)).

Calcitonins are found in a variety of vertebrate species including mammals, birds and fish. The hormone is secreted by the C cells, which are localized in the thyroid gland of mammals, and in the ultimobranchial glands in the lower vertebrates. Human calcitonin (hCT) has the following amino acid sequence:

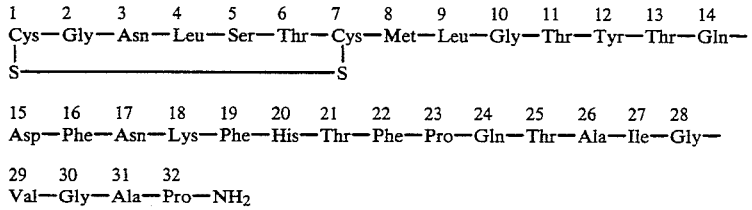

```
1      2     3     4     5     6     7     8     9    10    11    12    13    14
Cys— Gly— Asn— Leu— Ser— Thr— Cys— Met— Leu— Gly— Thr— Tyr— Thr— Gln—
 |                                 |
 S─────────────────────────────────S 15    16    17    18    19    20    21    22    23    24    25    26    27    28
Asp— Phe— Asn— Lys— Phe— His— Thr— Phe— Pro— Gln— Thr— Ala— Ile— Gly—

29    30    31    32
Val— Gly— Ala— Pro—NH2
```

Calcitonin shows considerable divergence in amino acid sequence between lower vertebrates and higher vertebrates, with highly conserved residues clustered at the two ends of the calcitonin molecule believed to be important for biological activity. For example, a 1-7 disulfide bridge and a C-terminal proline amide are invariate among all species. Several other invariate amino acid residues occur near the N-and C-terminal ends. The middle portion of the molecule, positions 10 to 27, which is thought to control the potency and duration of the peptide, is by contrast quite variable in amino acid composition. Breimer, L. H., MacIntyre, I., and Zaidi, M., *Biochem. J.* 255:377-390 (1988) have reviewed the structures and biological properties of calcitonin peptides from various species and this information is hereby incorporated by reference.

Natural calcitonin peptides vary widely in their potency in humans, those of certain nonhuman species appearing to be more potent than human calcitonin. Calcitonins that are ultimobranchial in origin, such as salmon, eel, and avian, are more potent than the thyroidal human or porcine calcitonins. Salmon, eel, porcine and human calcitonins are currently used clinically in humans for the treatment of Paget's disease, osteoporosis, hypercalcemias, including hypercalcemia of malignancy, and for bone pain.

The correlation of potency with the structure of the calcitonin peptides is not well understood. Improved potency may be due to an amino acid sequence which permits a peptide conformation that is more favorably bound to the hormone receptor (Marx et al., *Science* 178:998–1001 (1972). A conformation that is more flexible, a feature provided by smaller, less bulky amino acids, has been determined to affect biological activity (Epand et al., *Biochemistry* 25:1964–1968(1988)). The identical biological potencies of eel and salmon calcitonin may accordingly be explained on the basis of similar primary structures and similar flexibility.

An alternative basis for the relatively greater potency of nonhuman calcitonins may be that the amino acid sequences of these calcitonins, characteristic of particular species, offers greater resistance to metabolic degradation in the human body than human calcitonin, and for this reason has a more persistent effect (Habener et al., *Nature(London)* 232:91–92 (1971)). For example, salmon calcitonin remains potent for about six hours after administration, while human calcitonin remains potent for about two hours.

In spite of their higher potency, however, non-human calcitonins, such as the ultimobranchial calcitonins, are not entirely satisfactory for human clinical use, primarily because the variable, poorly conserved middle portion of these calcitonins acts as an immunogen in vivo. The resulting antibody production can therefore limit their usefulness.

Further, after administration to man by subcutaneous injection, all the natural calcitonins have a relatively short half life because, in spite of species differences which act to retard proteolysis by plasma enzymes, they are subject to rapid renal and tissue clearance as well.

It would be useful to have calcitonin peptides which are more effective in clinical use either because of greater stability in vivo, and/or higher potency and longer duration of action than the native hormones. It would also be useful to have calcitonin peptides which are less immunogenic than the native hormones. Furthermore, analogues with increased lipophilicity and hydrophobicity could have altered pharmacokinetics and possess improved parenteral, nasal or oral bioavailability.

Accordingly, it is an object of the invention to provide synthetic calcitonin peptides which are more effective and less antigenic in the treatment of human disease than native calcitonins from human and other species. It is also an object of the invention to provide methods for the synthesis of these calcitonin analogues.

SUMMARY OF THE INVENTION

The present invention relates to analogues of hypocalcemic peptides, their pharmaceutically acceptable salt forms or compositions thereof, processes for their preparation, and their use in treating disease in vertebrate animals.

According to one aspect of the invention there are provided synthetic peptides that are analogues of calcitonin peptides, possessing hypocalcemic calcitonin activity and having the formula $$Y^0-xCT$$

wherein Y is a moiety present at position 0, the $NH_2$-terminus of xCT, and is an aliphatic amino acid selected from the group consisting of L- or D-amino acids having a branched or unbranched alkyl side chain of 1 to 8 carbon atoms; L- or D-methionine; L- or D-threonine; L- or D-serine; or analogues thereof; and xCT represents the amino acid sequence of a native calcitonin, for example, human (hCT), salmon (sCT), eel (eCT), rat (rCT), porcine (pCT), bovine (bCT), ovine (oCT), chicken (cCT) or rabbit calcitonin. Preferred peptides are those wherein $y^0$ is Leu; particularly preferred are $(Leu^0)$-hCT; $(Leu^0)$-eCT; $(Leu^0)$-sCT; $(Leu^0)$-cCT; and $(Leu^0)$-rCT.

Another class of calcitonin analogues has the formula $$Y^8-xCT$$

wherein Y and xCT are as defined above. Preferred peptides are those wherein $Y^8$ is Leu; particularly preferred are $(Leu^8)$-hCT; $(Leu^8)$-bCT; $(Leu^8)$-cCT; $(Leu^8)$-eCT; $(Leu^8)$-oCT; $(Leu^8)$-pCT; $(Leu^8)$-rCT; $(Leu^8)$-sCT, wherein hCT, bCT, cCT, eCT, oCT, pCT, rCT, and sCT are as defined above.

The invention also includes calcitonin analogues having Y amino acid substitutions at both the 0- and 8-positions. Preferred peptides of this group are $(Leu^{0,8})$-bCT; $(Leu^{0,8})$-cCT; $(Leu^{0,8})$-eCT; $(Leu^{0,8})$-hCT; $(Leu^{0,8})$-oCT; $(Leu^{0,8})$-pCT; $(Leu^{0,8})$-rCT; $(Leu^{0,8})$-sCT. According to yet another aspect of the invention there are provided calcitonin peptide analogues having a $Y^0$ or a $Y^8$ amino acid substitution or having Y amino acid substitutions at both the 0- and 8-positions wherein there is at least one additional Y amino acid substitution at positions 4, 12, 16, 21, or 27. Preferred peptides of this group are $Leu^{0,8,12}$)-hCT; $(Leu^{0,8,12,16})$-hCT; $(Leu^{0,8,16})$-hCT; $(Leu^{0,12})$-hCT; $(Leu^{0,16})$-hCT; $(Leu^{0,12,16})$-hCT; $(Leu^{8,12})$-hCT; $(Leu^{8,12,16})$-hCT; $(Leu^{8,16})$-hCT; or $(Leu^{12,16})$-hCT, wherein hCT represents the amino acid sequence of human calcitonin.

In all of the calcitonin analogues disclosed, Y is preferably selected from the group consisting of Gly, Ala, Leu, Ile, Val, Thr, Nor-Leu, Nor-Val, Met, or Sero. Leu is particularly preferred.

According to another aspect of the invention there are provided calcitonin analogues having $Y^0$ additions or $Y^8$ substitutions, or the same substitutions together with Y substitutions at positions 4, 12, 16, 21, or 27, wherein xCT represents a calcitonin sequence in which one or more of the amino acid residues at positions 19 through 22 are deleted. Preferred peptides among this group are $(Leu^{0,8}, des(19))$-hCT; $(Leu^{0,8}, des(19-22))$-hCT; $(Leu^{0,8,12}, des(19))$-hCT; $(Leu^{0,8,12}, des(19-22))$-hCT; $(Leu^{0,8,12,16}, des(19))$-hCT; $(Leu^{0,8,12,16}, des(19-22))$-hCT; $(Leu^{0,8}, des(19))$-eCT; $(Leu^{0,8}, des(19-22))$-eCT; $(Leu^{0,8}, des(19))$-sCT; $(Leu^{0,8}, des(19-22))$-sCT; $(Leu^{0,8}, des(19))$-eCT; and $(Leu^{0,8}, des(19-22))$-eCT, wherein hCT is human calcitonin, eCT is eel calcitonin, and sCT is salmon calcitonin.

According to yet another aspect of the invention, there are provided pharmaceutical formulations comprising an effective therapeutic amount of at least one of the calcitonin analogues of the invention in combination with a pharmaceutically acceptable carrier.

The invention further provides methods for treating disease, comprising the use of the disclosed calcitonin analogues. A method provided for treating hypercalcemia comprises the steps of administering to said mammal in need of such treatment an effective, blood calcium-reducing amount of a synthetic calcitonin peptide of the invention. A method provided for treating Paget's disease or osteoporosis comprises administering to an affected subject a bone resorption-opposing amount of a synthetic calcitonin analogue of the invention for a period sufficient to reduce or eliminate the resorption of bone.

Yet another therapeutic method of the invention is directed to treating bone pain associated with osteoporosis, osteoporotic fractures, Paget's disease, and the osteolysis of malignancy, comprising administering to a patient experiencing bone pain associated with the diseases described, a pain-relieving amount of at least one of the synthetic calcitonin analogues of the invention.

DETAILED DESCRIPTION OF THE INVENTION

Hypocalcemic peptides that are analogues of native calcitonins but in which amino acid residues are added, substituted, or deleted have been synthesized and these calcitonin analogues provide a biological response that is more potent in both the native species and foreign species than that of the native calcitonin peptide. Preferred calcitonin analogues are particularly those species that are more potent in humans than native human calcitonin itself.

The calcitonin peptides of the invention possess valuable pharmacological properties. They can used to lower the serum plasma calcium level in patients suffering from diseases associated with elevated serum levels of calcium such as, for example, the hypercalcemia of malignancy, as well as for treating Paget's disease and osteoporosis, particularly of the senile type. Use of synthetic calcitonin analogues of the invention also reduce the immunogenic activity normally experienced with the use of native calcitonins of non-human species in humans. Similar calcitonin peptides are known, for example, from co-pending application Ser. No. 07/446,932, filed Dec. 6, 1989 and 07/572,674, filed Aug. 24, 1990. However, the calcitonin analogues of the present invention all contain an additional aliphatic amino acid, Y, at the 0-position, that is, attached to the NH$_2$-terminal residue of a native calcitonin, xCT, or they contain an aliphatic amino acid, Y, substituted at the 8-position of a native calcitonin, xCT.

The Y$^0$ calcitonin analogues can also have a substituted aliphatic amino acid residue, Y, at positions 4, 8, 12, 16, 21, or 27; similarly the Y$^8$ calcitonin analogues can also have a substituted aliphatic amino acid residue, Y, at positions 4, 12, 16, 21, or 27.

Y is preferably L- or D-leucine (Leu) but is also an aliphatic amino acid selected from the group consisting of any L- or D-amino acid having a branched or unbranched alkyl side chain of 1 to 8 carbon atoms, for example, glycine, alanine, $\beta$-alanine, valine, norvaline, $\alpha$-amino-n-butyric acid, $\gamma$-amino-n-butyric acid, $\beta$-amino-isobutyric acid, isoleucine, norleucine, methionine, threonine, serine, homoserine; or analogues thereof.

Hereinafter, these synthetic calcitonin analogues will be referred to as the calcitonin peptides of the invention.

Preferred calcitonin peptides of the invention are those having the formula (Leu$^0$)—xCT or (Leu$^8$)—xCT xCT is preferably human calcitonin, but is also salmon (sCT), eel (eCT), rat (rCT), bovine (bCT), ovine (oCT), porcine (pCT), chicken (cCT) or rabbit calcitonin.

It has been suggested that conformational flexibility of a calcitonin peptide can enhance its biological effectiveness (Epand, R. M., et al. *Biochemistry* 25:1964–1968 (1986)). Flexibility has been shown to be improved where bulky residues, which promote the formation of rigid helices, are absent (Kaiser, E. T. and Kedzi, F. J., *Science* 223:249–255 (1984).

The calcitonin analogues of the invention therefore include hypocalcemic peptides, corresponding in part to native calcitonins, and having the addition of a Y amino acid at position 0 and/or the substitution of a Y amino acid at position 8, in which flexibility has been improved by replacement of some amino acid residues by a variety of less bulky moieties. Accordingly, amino acid residues corresponding to those of native calcitonins at positions 4, 12, 16, and 27 have been replaced in this group of calcitonin analogues of the invention by leucine.

Particularly preferred calcitonin peptides of this type are: (Leu$^0$)-hCT; (Leu$^{0,8}$)-hCT; (Leu$^{0,8,12}$)-hCT; (Leu$^{0,8,12,16}$)-hCT; (Leu$^{8,12}$)-hCT; (Leu$^{8,12,16}$)-hCT; (Leu$^{8,16}$)-hCT; (Leu$^{12,16}$)-hCT, (Leu$^{0,12}$)-hCT; (Leu$^{0,12,16}$)-hCT; (Leu$^{0,16}$)-hCT; and (Leu$^{0,8,16}$)-hCT, wherein hCT represents the amino acid sequence of human calcitonin.

In a second group of calcitonin peptide analogues of this type, the flexibility of the peptide chain is increased by the elimination of certain amino acid residues. For example, the amino acid sequence comprising residues 19–22 is shown to be non-essential for biological activity; therefore one group of calcitonin peptides according to the invention comprises hypocalcemic peptides in which at least one and as many as all of these residues of native calcitonin have been eliminated. Accordingly, any of the Y$^0$ and the Y$^8$ calcitonin analogues disclosed above can further have deletions of amino acids at positions 19, 20, 21, and 22.

Preferred calcitonin analogues of this type are: [Y$^0$, des(19)]-xCT, [Y$^0$, des(19–22)]-xCT, [Y$^{0,8}$, des(19)]-xCT, [Y$^{0,8}$, des(19–22)]-xCT, [Y$^{0,8,12}$, des(19)]-hCT, [Y$^{0,8,12}$, des(19–22)]-hCT, [Y$^{0,8,12,16}$, des(19)]-hCT, [Y$^{0,8,12,16}$, des(19–22)]-hCT, [Y$^8$, des(19)]-xCT, [Y$^8$, des(19–22)]-xCT, [Y$^{8,12}$, des(19)]-hCT, [Y$^{8,12}$, des(19–22)]-hCT, [Y$^{8,12,16}$, des(22)]-hCT and [Y$^{8,12,16}$, des(19–22)]-hCT.

All known natural calcitonins are polypeptides containing a sequence of 32 amino acids. The position of the each amino acid involved in the calcitonin peptide chain is numbered according to the accepted procedure, beginning at position 1 for Cys on one end of the chain and ending with Pro at position 32 at the other end. This same numbering system is applied to any calcitonin peptide chain even if it contains less that the 32 amino acid units present in the naturally-occurring calcitonins. The amino acid abbreviations used are those commonly employed in the peptide art and described in the literature, e.g. IUPAC-IUB Commission on Biochemical Nomenclature, *J. Biol. Chem.* 247, 979–982 (1972). Human calcitonin comprises the presently known human calcitonin sequence. Amino acids discussed herein are of the L-form unless otherwise mentioned.

Calcitonin peptides of the invention containing basic amino acids such as lysine, arginine, and histidine may exist in the form of salts such as chloride, acetate, phosphate, citrate, succinate, oxalate, etc. Acetate and hydrochloride salt forms are particularly preferred. For the purposes of this invention, peptides of the invention and their acid addition salts are considered to be one and the same.

Calcitonins lower the blood calcium of immature rats by inhibiting bone resorption. Their potency can be therefore be assessed by determining the micrograms of peptide required to reduce the serum calcium of the test animal by ten percent. The results of in vivo tests of the biological activities of synthetic calcitonin peptides of the invention are shown in Examples 30 and 31. All of the peptides tested were superior to native human calcitonin in their potency, duration of action, or both.

Therapeutic Applications

The hypocalcemic calcitonin peptides of the invention offer many advantages over natural calcitonins in the treatment of disease. Their principal advantage is that they provide increased potency in comparison to native calcitonins. For example, $Leu^{0,8,12}$-hCT has a biological activity substantially equivalent to a salmon calcitonin sequence while retaining an amino acid sequence similar to that of native human calcitonin.

The invention therefore also relates to the use of the calcitonin peptides of the invention and their physiologically acceptable salts for the preparation of pharmaceutical formulations which can be employed as medicaments in human and veterinary medicine. For this purpose, it is possible to convert them into a form suitable for administration together with at least one vehicle or auxiliary. Suitable vehicles are organic and inorganic substances which are suitable for enteral (for example, oral), parenteral, topical, transdermal or nasal administration and which do not react with the calcitonin peptides. The indicated formulations can be sterilized and/or contain auxiliaries, such as lubricants, preservatives stabilizers, wetting agents, emulsifiers, buffers, colorings and flavoring.

The active peptides may be administered parenterally, that is by subcutaneous, intramuscular, or intravenous injection. The pharmaceutical formulations suitable for injectable use include aqueous solutions or dispersions and powders for the extemporaneous preparation of injectable solutions or dispersions. It is possible also to freeze-dry the calcitonin peptides and to use the lyophilizates obtained, for example, for the preparation of products for injection. In all cases, the form must be sterile and the solution must be fluid to the extent that easy syringability exists. It must be stable under the conditions of manufacture and storage and must be preserved against contaminations of microorganisms, such as for example, bacteria and fungi. The carrier can be a solvent or a dispersion medium containing, for example, water, or a polyol such as glycerol, and suitable mixtures thereof. Compositions for intramuscular use may also contain minor amounts of salts, acids, and bases to adjust tonicity and buffer the solution. Suitable buffering and isotonicity agents are readily determinable by persons skilled in the art.

Oral or nasal administration is also possible especially with analogues which have increased lipophilicity. Formulations for oral ingestion are in the form of tablets, capsules, pills, ampoules of powdered active agent, or oily or aqueous suspensions or solutions. Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract. Such oral compositions and preparations should contain at least 0.1% of active peptide, although the percentages of the compositions may vary widely. The amount of therapeutically active compound in such compositions is such that a suitable dosage will be obtained in a convenient volume for ingestion.

Liposomal preparations of calcitonin peptides are also useful in enhancing the oral administration as disclosed in U.S. Pat. No. 4,692,433, entitled "Method and Composition for Regulating the Serum Calcium Levels of Mammals," which is hereby incorporated by reference.

Formulations for nasal administration may be in the form of liquids and optionally may contain absorption promoting substances, for example, a lactone of a water-soluble organic acid, and other compounds of similar function well known to those trained in the art. The nasal formulations may also be in the form of an aerosol comprising the calcitonin peptide together with an extender which may be an amino acid, for example, methionine. Powdery nasal formulations, such as those disclosed by Y. Suzuki et al, U.S. Pat. No. 4,613,500, are also useful ways to administer the subject calcitonin peptides. The formulation can be packaged in a device to provide a metered spray, propelled either manually or by use of a propellant, such as a chlorofluorocarbon or a compressed gas.

Transdermal application formulations can comprise the calcitonin peptides, optionally incorporated into a suitable topical carrier, or a dermal patch. The calcitonins can be combined with a penetration-enhancing agent, for example, dimethylsulfoxide (DMSO), dimethylformamide, dimethylacetamide, or Azone® azacycloheptane-2-one Both topical carriers and the use of penetration enhancers are disclosed by Blaug, S., Chap. 87 *Remington's Pharmaceutical Sciences*, 15th Ed. Mack Publishing Co., Easton, Pa. 18042 (1975).

The invention also relates to the use of the calcitonin peptides of the invention for the therapeutic treatment of the human or animal body and for the control of illnesses wherein a reduction or normalization of serum calcium is sought, or to influence bone metabolism, as in the treatment of hyperparathyroidism, Vitamin D intoxication, idiopathic hypercalcemia of infancy, bone fracture, osteomalacia, rickets, renal osteodystrophy, Paget's disease, osteoporosis of diverse etiologies, especially common senile type, neurodystrophy, osteolytic bone metastases, and bone pain associated with any of these diseases, as well as that of articular rheumatism. The calcitonin peptides also inhibit gastric secretion and are therefore useful for the treatment of acute pancreatitis and gastrointestinal disorders, especially gastric ulcers.

These hypocalcemic peptides are administered in amounts ranging from 0.05 to 100 International Units (IU) per kg body weight per day, analogously to known therapeutic calcitonins. A preferred dosage for optimum results would be 0.2 to 10 IU/kg/day. The peptide may be given as few as one or two days a week or as often as twice daily. It will be appreciated that the actual preferred amounts of active compound in a specific case will vary according to the specific calcitonin peptide being utilized, the particular formulation, and the particular disorder being treated. The dosage regimen for a particular subject can be determined using conventional considerations, including the clinical indication. For treating the hypercalcemia of malignancy, somewhat higher dosages may be required (5 to 20 IU/kg/day) than with Paget's disease, osteoporosis and bone pain (0.2 to 2 IU/kg/day). Oral, nasal, and transdermal administration will require dosages 1.5 to 100 times higher.

The chemical reactions described below are generally disclosed in terms of their general application to the preparation of the calcitonin peptides of the invention. Occasionally, the reaction may not be applicable as described to each peptide included within the disclosed scope. The peptides for which this occurs will be readily recognized by those skilled in the art. In all such cases, either the reactions can be successfully performed by conventional modifications known to those skilled in the art, e.g. by appropriate protection of interfering groups, by changing to alternative conventional reagents, or by routine modification of reaction conditions. Alternatively, other reactions disclosed herein or otherwise conventional will be applicable to the preparation of the corresponding calcitonin peptides of the invention. In all preparative methods, all starting materials are known or readily preparable from known starting materials.

Peptide Synthesis: Hypocalcemic peptides of this invention may be synthesized according to a solid phase method, solution phase method, or by genetic engineering. Solution phase method and especially the solid phase methods are particularly preferred. These methods are well known to those skilled in the art and described in detail in the literature; e.g. Barany, G. and R. B. Merrifield, in *The Peptides*, Vol. 2; E. Gross & J. Meienhoffer, eds.; Academic Press, New York, pp. 3–284 (1979). Synthesis of peptides such as calcitonin which contain a C-terminal amide group is preferably carried out on a 4-methylbenzhydrylamine-divinylbenzene-copolystyrene, referred to as MBHA resin is commercially available from supply houses, and its preparation and application in SPPS are well documented in the field, see Pietta, P. G. and G. R. Marshall, J. Chem. Soc. D, 650–651 (1970), and Channabasavaiah, K. & J. M. Stewart, *Biochem. Biophys. Res. Commun.* 86, 1266–1273, (1979). Peptides described in this invention are prepared starting from t-butyloxycarbonyl-proline linked to MBHA resin (Boc-Pro-MBHA) which is also commercially available. Boc-Pro-MBHA resin is treated with anhydrous trifluoroacetic acid (TFA or 25 to 75% mixture of TFA in dichloromethane (TFA-DCM) to deprotect the amino group, and the resulting salt neutralized using 5 to 20% triethylamine in DCM (TEA-DCM) or 5 to 20% diisopropylethylamine in DCM (DIEA-DCM) to furnish H2N-Pro-MBHA resin. Next amino acid in the sequence (AA31) containing appropriate protecting groups is coupled to H2N-Pro-MBHA resin using N,N'-dicyclohexylcarbodiimide (DCC) and N-hydroxybenzotriazole (HOBt). The coupling reaction is carried out for a period of 1 to 18 hr and in an appropriate solvent such as toluene, dichloromethane (DCM), dimethylformamide (DMF) or tetrahydrofuran (THF), or mixtures thereof. The desired peptide chain is assembled by repeating the deprotection, neutralization and coupling reactions using appropriate amino acid derivatives, successively. It is generally known to those skilled in the art that amino acids contain more than one reactive functional group and it is necessary to mask one or more of these groups which are not intended to participate in various steps of SPPS. Commercially available derivatized amino acids used for the SPPS of various peptides described in this invention ere: Boc-Ala-OH, Boc-Arg(Tos)-OH, Boc-Asn-OH, Boc-Asp(O-cyclohexyl)-OH, Boc-Asp(OBzl)-OH, Boc-Cys(S-4-MeBzl)-OH, Boc-Gln-OH, Boc-Glu(O-cyclohexyl)-OH, Boc-Glu(OBzl)-OH, Boc-Gly-OH, Boc-His(Tos)-OH, Boc-His(Bom)-OH, Boc-Ile-OH, Boc-Leu-OH, Boc-Lys(Cl-Z)-OH, Boc-Norleucine, Boc-Norvaline, Boc-Met-OH, Boc-Phe-OH, Boc-Pro-OH, Boc-Ser(Bzl)-OH, Boc-Thr(Bzl)-OH, Boc-Thr(Bzl)-OH, Boc-Trp-OH, Boc-Trp(Formyl)-OH, Boc-Tyr(Br-Z)-OH, and Boc-Val-OH. After the synthesis, the peptide resin is treated with hydrogen fluoride to release the peptide which is further purified by chromatography.

It is believed that one skilled in the art can, using the preceding description, utilize the invention to its fullest extent. The present invention is described below in detail using the following examples, but the methods described are applicable for the preparation of all the peptides described and are not limited to the examples given below.

The following preferred embodiments are, therefore, to be construed as merely illustrative and not limitative for the remainder of the disclosure in any way whatsoever. In the following examples, all temperatures are set forth uncorrected in degrees Celsius; unless otherwise indicated, all parts and percentages are by weight.

EXAMPLE 1

Synthesis of [Leu$^{0,8,12,16}$]-hCT

```
 0    1    2    3    4    5    6    7    8    9   10   11   12   13   14
Leu—Cys—Gly—Asn—Leu—Ser—Thr—Cys—Leu—Leu—Gly—Thr—Leu—Thr—Gln—
     |                       |
     S———————————————————————S 15   16   17   18   19   20   21   22   23   24   25   26   27   28   29
Asp—Phe—Asn—Lys—Phe—His—Thr—Phe—Pro—Gln—Thr—Ala—Ile—Gly—Val—

30   31   32
Gly—Ala—Pro—NH2
```

Resin Peptide Synthesis: Boc-Pro-MBHA Resin (2 g, 1 mmol) placed in a reaction vessel of Beckman 990 B Peptide Synthesizer (Beckman Instruments, Palo Alto, Calif.) and subjected to the following operations. Each step is carried out one time unless specified otherwise, and reagents and solvents after each step are separated from the peptide resin by filtration under nitrogen.

| Step | Reagent/solvent/No of times | Mix Time (minutes) |
|---|---|---|
| 1 | DCM (30 ml, 3 times) | 1.5 |
| 2 | TFA-DCM (1:1) (30 ml) | 1.5 |

-continued

| Step | Reagent/solvent/No of times | Mix Time (minutes) |
|---|---|---|
| 3 | TFA-DCM (1:1) (30 ml) | 30.0 |
| 4 | DCM (30 ml, 3 times) | 1.5 |
| 5 | Methanol (30 ml, 3 times) | 1.5 |
| 6 | DCM (30 ml, 3 times) | 1.5 |
| 7 | TFA-DCM (1:1) (30 ml) | 1.5 |
| 8 | TFA-DCM (1:1) (30 ml) | 5.0 |
| 9 | DCM (30 ml, 3 times) | 1.5 |
| 10 | DMF (30 ml, 3 times) | 1.5 |
| 11 | Boc-Thr(Bzl)-OH/HOBt/DCC (4 mmol each) in DMF (20 ml) | 240.0* |
| 12 | (30 ml, 3 times) | 1.5 |
| 13 | Methanol (30 ml, 3 times) | 1.5 |
| 14 | DCM (30 ml, 3 times) | 1.5 |

*Coupling reation was carried out for an average of 4 hours, as in this case, or until a ninhydrin test (Kaiser E.T. et al, Anal. Biochem. 34, 595–8, 1969) showed a negative result indicating the absence of free amino groups. The same sequence of reations was repeated using appropriate amino acid derivatives until the required peptide chain was assembled on the resin. After completion of the synthesis, the resin was removed from the vessel and dried under vacuum.

Cleavage of the Resin-Peptide using Hydrogen Fluoride (HF):

The dried peptide resin (1 g), anisole (1 ml) and p-cresol (0.1 g) were placed in a Kel F reaction vessel. The vessel was placed in a bath of liquid nitrogen and anhydrous HF (15 ml) was condensed into the vessel. The reaction mixture was stirred at $-10°$ C. for 1 hour and HF was removed by evaporation under vacuum. The residue was triturated with dry ether (50 ml), filtered and washed with additional quantity of ether (3×50 ml). Peptide product in the mixture was isolated by extracting with glacial acetic acid (3×50 ml) followed by lyophilization of the solvent.

Disulfide bond formation: The linear peptide which contains free sulfhydryl groups in the cysteine residues at positions 1 and 7 was dissolved in distilled water (1 mg per 5 ml) and subjected to air oxidation at pH 7.5 for 24 hours. The solution was filtered to remove insoluble material and the filtrate was lyophilized to obtain the product as a white powder. Other procedures, such as oxidation with iodine or potassium ferricyanide can also be used.

Peptide Purification: Peptide powder obtained above (200 mg) was dissolved in 1N acetic acid (3 ml), loaded to a Sephadex G-25 (superfine) column (1.5 cm×100 cm) and eluted with 1N acetic acid. The eluent fractions containing the peptide were pooled and freeze dried. The resulting peptide (50 mg) was further purified by preparative reverse phase high performance chromatography (RP-HPLC) using a Waters C-4 column and a buffer gradient of 0.1% TFA in water to 70% acetonitrile in 0.1% TFA in water. The fractions containing pure peptide (determined by analytical HPLC) were combined and the product isolated by lyophilization. Purity of the peptide was better than 95% by HPLC; and amino acid analysis followed by acid hydrolysis (6N HCl, 110° C., 24 hr) gave expected amino acid ratios.

EXAMPLE 1a: [$Val^0$, $Leu^{8,12,16}$]-hCT; EXAMPLE 1b: [$Ile^0$, $Leu^{8,12,16}$]-hCT; EXAMPLE 1c: [$Met^0$, $Leu^{8,12,16}$]-hCT; EXAMPLE 1d: [$Thr^0$, $Leu^{8,12,16}$]-hCT; EXAMPLE 1e: [$Ser^0$, $Leu^{8,12,16}$]-hCT; EXAMPLE 1f: [$Ala^0$, $Leu^{8,12,16}$]-hCT; EXAMPLE 1g: [Norvaline$^0$, $Leu^{8,12,16}$]-hCT; and EXAMPLE 1h: [Norleucine$^0$, $Leu^{8,12,16}$]-hCT; were prepared according the above method except for using appropriate amino acid derivatives during the last coupling cycle.

EXAMPLE 1i: [$Leu^{0,8,12,16}$, des(19)]-hCT; EXAMPLE 1j: [$Leu^{0,8,12,16}$, des(19–22)]-hCT; EXAMPLE 1k: [$Val^0$, $Leu^{8,12,16}$, des(19)]-hCT; EXAMPLE 1l: [$Val^0$, $Leu^{8,12,16}$, des(19–22)]-hCT; EXAMPLE 1m: [$Ile^0$, $Leu^{8,12,16}$, des(19–22)]-hCT; EXAMPLE 1n: [$Ile^0$, $Leu^{8,12,16}$, des(19)]-hCT; EXAMPLE 1o: [$Met^0$, $Leu^{8,12,16}$, des(19–22)]-hCT; EXAMPLE 1p: [$Met^0$, $Leu^{8,12,16}$, des(19)]-hCT; EXAMPLE 1q: [$Thr^0$, $Leu^{8,12,16}$, des (19)]-hCT; EXAMPLE 1r: [$Thr^0$, $Leu^{8,12,16}$, des(19–22)]-hCT; EXAMPLE 1s: [$Ser^0$, $Leu^{8,12,16}$, des(19)]-hCT; EXAMPLE 1t: [$Ser^0$, $Leu^{8,12,16}$, des (19–22)]-hCT; EXAMPLE 1u: [$Ala^0$, $Leu^{8,12,16}$, des(19)]-hCT; EXAMPLE 1v: [$Ala^0$, $Leu^{8,12,16}$, des(19–22)]-hCT; EXAMPLE 1w: [Norvaline$^0$, $Leu^{8,12,16}$, des(19)]-hCT; EXAMPLE 1x: [Norvaline$^0$, $Leu^{8,12,16}$, des(19–22)]-hCT; EXAMPLE 1y: [Norleucine$^0$, $Leu^{8,12,16}$, des(19)]-hCT; and EXAMPLE 1z: [Norleucine$^0$, $Leu^{8,12,16}$, des (19–22)]-hCT were prepared according the above method except for eliminating the coupling cycles for amino acid 19 or 19 through 22 as indicated.

EXAMPLE 2

Synthesis of [$Leu^{0,8,12}$]-hCT

```
 0    1    2    3    4    5    6    7    8    9   10   11   12   13   14
Leu—Cys—Gly—Asn—Leu—Ser—Thr—Cys—Leu—Leu—Gly—Thr—Leu—Thr—Gln—
    |                       |
    S———————————————————————S 15   16   17   18   19   20   21   22   23   24   25   26   27   28   29
Asp—Phe—Asn—Lys—Phe—His—Thr—Phe—Pro—Gln—Thr—Ala—Ile—Gly—Val—

30   31   32
Gly—Ala—Pro—NH2
```

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 2a: [$Val^0$, $Leu^{8,12}$]-hCT; EXAMPLE 2b: [$Ile^0$, $Leu^{8,12}$]-hCT; EXAMPLE 2c: [$Met^0$, $Leu^{8,12}$]-hCT; EXAMPLE 2d: [$Thr^0$, $Leu^{8,12}$]-hCT; EXAMPLE 2e: [$Ser^0$, $Leu^{8,12}$]-hCT; EXAMPLE 2f: [$Ala^0$, $Leu^{8,12}$]-hCT; EXAMPLE 2g: [Norvaline$^0$, $Leu^{8,12}$]-hCT; and EXAMPLE 2h: [Norleucine$^0$, $Leu^{8,12}$]-hCT; were prepared according the above method except for using appropriate amino acid derivatives during the last coupling cycle.

EXAMPLE 2i: [$Leu^{0,8,12}$, des (19)]-hCT; EXAMPLE 2j: [$Leu^{0,8,12}$, des(19–22)]-hCT; EXAMPLE 2k: [$Val^0$, $Leu^{8,12}$, des(19)]-hCT; EXAMPLE 2l: [$Val^0$, $Leu^{8,12}$, des(19–22)]-hCT; EXAMPLE 2m: [$Ile^0$, $Leu^{8,12}$, des(19)]-hCT; EXAMPLE 2n: [$Ile^0$, $Leu^{8,12}$, des(19–22)]-hCT; EXAMPLE 2o: [$Met^0$, $Leu^{8,12}$, des (19)]-hCT; EXAMPLE 2p: [$Met^0$, $Leu^{8,12}$, des(19–22)]- hCT; EXAMPLE 2q: [Thr⁰, Leu⁸,¹², des(19)]-hCT; EXAMPLE 2r: [Thr⁰, Leu⁸,¹², des(19-22)]-hCT; EXAMPLE 2s: [Ser⁰, Leu⁸,¹², des(19)]-hCT; EXAMPLE 2t: [Ser⁰, Leu⁸,¹², des(19-22)]-hCT; EXAMPLE 2u: [Ala⁰, Leu⁸,¹², des(19)]-hCT; EXAMPLE 2v: [Ala⁰, Leu⁸,¹², des(19-22)]-hCT; EXAMPLE 2w: [Norvaline⁰, Leu⁸,¹², des(19)]-hCT; EXAMPLE 2x: [Norvaline⁰, Leu⁸,¹², des (19-22)]-hCT; EXAMPLE 2y: [Norleucine⁰, Leu⁸,¹², des(19)]-hCT; and EXAMPLE 2z: [Norleucine⁰, Leu⁸,¹², des(19)]-hCT were prepared according the above method except for eliminating the coupling cycles for amino acid 19 or 19 through 22 as indicated.

EXAMPLE 3

Synthesis of [Leu⁰,⁸]-hCT

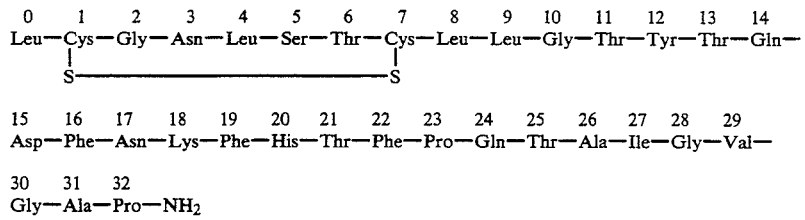

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 3a: [Val⁰, Leu⁸]-hCT; EXAMPLE 3b: [Ile⁰, Leu⁸]-hCT; EXAMPLE 3c: [Met⁰, Leu⁸]-hCT; EXAMPLE 3d: [Thr⁰, Leu⁸]-hCT; EXAMPLE 3e: [Ser⁰, Leu⁸]-hCT; EXAMPLE 3f: [Ala⁰, Leu⁸]-hCT; EXAMPLE 3g: [Norvaline⁰, Leu⁸]-hCT; and EXAMPLE 3h: [Norleucine⁰, Leu⁸]-hCT; were prepared according the above method except for using appropriate amino acid derivatives during the last coupling cycle.

EXAMPLE 3i: [Leu⁰,⁸, des(19)]-hCT; EXAMPLE 3j: [Leu⁰,⁸, des(19-22)]-hCT; EXAMPLE 3k: [Val⁰, Leu⁸, des(19)]-hCT; EXAMPLE 3l, [Val⁰, Leu⁸, des(19-22)]-hCT; EXAMPLE 3m: [Ile⁰, Leu⁸, des(19)]-hCT; EXAMPLE 3n: [Ile⁰, Leu⁸, des(19-22)]-hCT; EXAMPLE 3o: [Met⁰, Leu⁸, des (19)]-hCT; EXAMPLE 3p: [Met⁰, Leu⁸, des(19-22)]-hCT; EXAMPLE 3q: [Thr⁰, Leu⁸, des(19)]-hCT; EXAMPLE 3r: [Thr⁰, Leu⁸, des(19-22)]-hCT; EXAMPLE 3s: [Ser⁰, Leu⁸, des(19)]-hCT; EXAMPLE 3t: [Ser⁰, Leu⁸, des(19-22)]-hCT; EXAMPLE 3u: [Ala⁰, Leu⁸, des(19)]-hCT; EXAMPLE 3v: [Ala⁰, Leu⁸, des(19-22)]-hCT; EXAMPLE 3w: [Norvaline⁰, Leu⁸, des(19)]-hCT; EXAMPLE 3x: [Norvaline⁰, Leu⁸, des(19-22)]-hCT; EXAMPLE 3y: [Norleucine⁰, Leu⁸, des(19)]-hCT; and EXAMPLE 3z: [Norleucine⁰, Leu⁸, des(19)]-hCT were prepared according the above method except for eliminating the coupling cycles for amino acid 19 or 19 through 22 as indicated.

EXAMPLE 4

Synthesis of [Leu⁰]-hCT

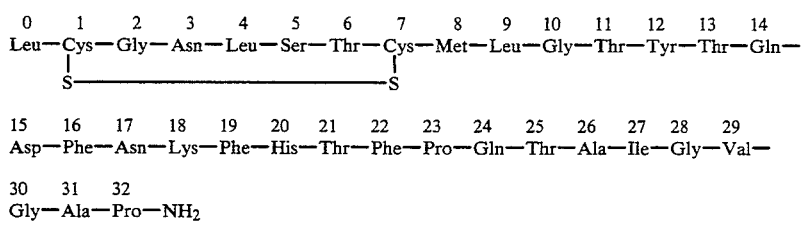

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 4a: [Val⁰]-hCT; EXAMPLE 4b: [Ile⁰]-hCT; EXAMPLE 4c: [Met⁰]-hCT; EXAMPLE 4d: [Thr⁰]-hCT; EXAMPLE 4e: [Ser⁰]-hCT; EXAMPLE 4f: [Ala⁰]-hCT; EXAMPLE 4g: [Norvaline⁰]-hCT; and EXAMPLE 4h: [Norleucine⁰]-hCT; were prepared according the above method except for using appropriate amino acid derivatives during the last coupling cycle.

EXAMPLE 5

Synthesis of [Leu⁸,¹²,¹⁶]-hCT

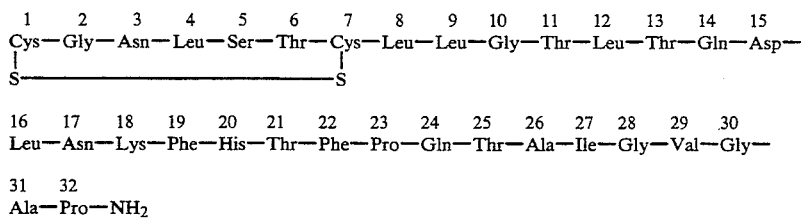

Starting from Boc-Pro-MBHA resin (2 g, 1 mmol), the title peptide was synthesized using appropriate amino acid derivatives. The resin is then filtered, dried under vacuum. Cleavage of the peptide from the resin,

EXAMPLE 6
Synthesis of [Leu$^{8,12}$]-hCT

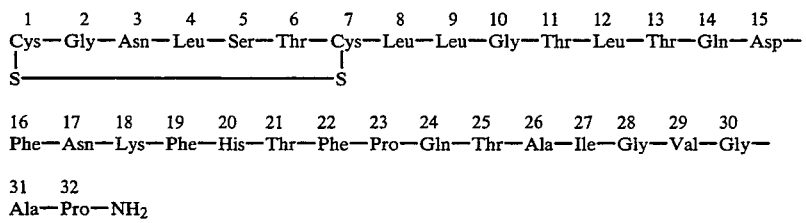

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 7
Synthesis of [Leu$^8$]-hCT

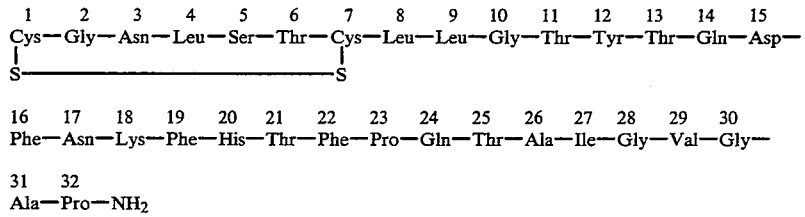

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 8
Synthesis of [Leu$^{8,16}$]-hCT

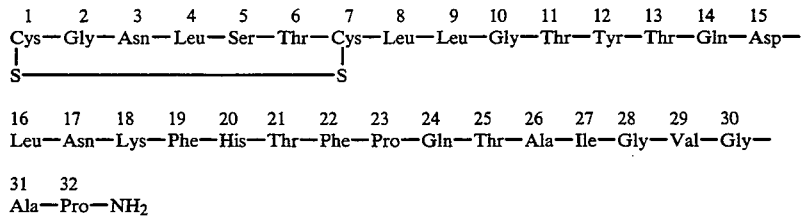

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 9
Synthesis of [Leu$^{0,12,16}$]-hCT

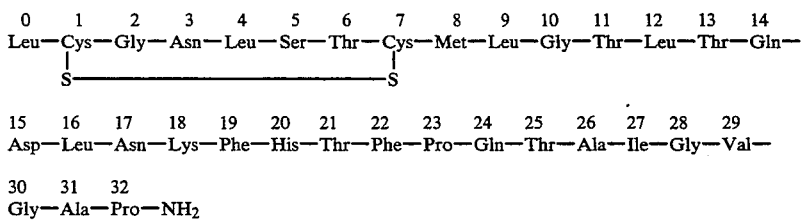

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 10
Synthesis of Leu$^{0,16}$]-hCT

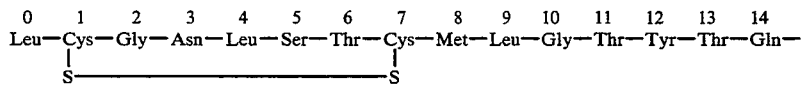

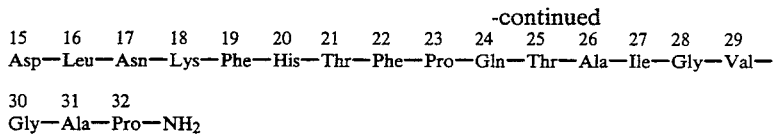

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 10a: [Val⁰, Leu⁸,¹⁶]-hCT; EXAMPLE 10b: [Ile⁰, Leu⁸,¹⁶]-hCT; EXAMPLE 10c: [Met⁰, Leu⁸,¹⁶]-hCT; EXAMPLE 10d: [Thr⁰, Leu⁸,¹⁶]-hCT; EXAMPLE 10e: [Ser⁰, Leu⁸,¹⁶]-hCT; EXAMPLE 10f: [Ala⁰, Leu⁸,¹⁶]-hCT; EXAMPLE 10g: [Norvaline⁰, Leu⁸,¹⁶]-hCT; and EXAMPLE 10h: [Norleucine⁰, Leu⁸,¹⁶]-hCT; were prepared according the above method except for using appropriate amino acid derivatives during the last coupling cycle.

EXAMPLE 11

Synthesis of [Leu⁰,¹²]-hCT

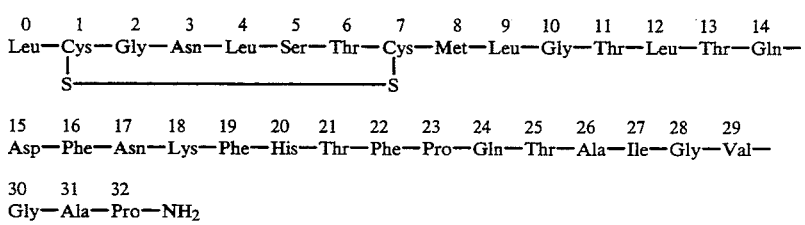

Starting from Boc-Pro-MBHA resin (2 g, 1 mmol), the title peptide was synthesized using appropriate amino acid derivatives. The resin is then filtered, dried under vacuum. Cleavage of the peptide from the resin, purification and characterization is carried out as described in Example 1.

EXAMPLE 11a: [Val⁰, Leu¹²]-hCT; EXAMPLE 11b: [Ile⁰, Leu¹²]-hCT; EXAMPLE 11c: [Met⁰, Leu¹²]-hCT; EXAMPLE 11d: [Thr⁰, Leu¹²]-hCT; EXAMPLE 11e: [Ser⁰, Leu¹²]-hCT; EXAMPLE 11f: [Ala⁰, Leu¹²]-hCT; EXAMPLE 11g: [Norvaline⁰, Leu¹²]-hCT; and EXAMPLE 11h: [Norleucine⁰, Leu¹²]-hCT; were prepared according the above method except for using appropriate amino acid derivatives during the last coupling cycle.

EXAMPLE 12

Synthesis of [Leu⁸]-eCT

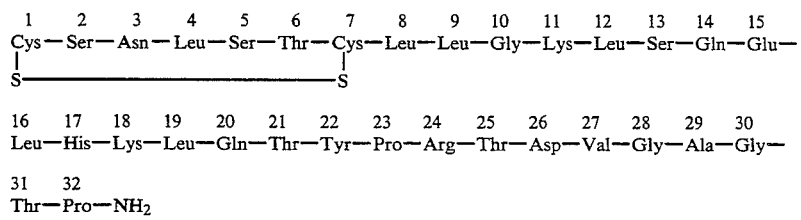

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 13

Synthesis of [Leu⁰,⁸]-eCT

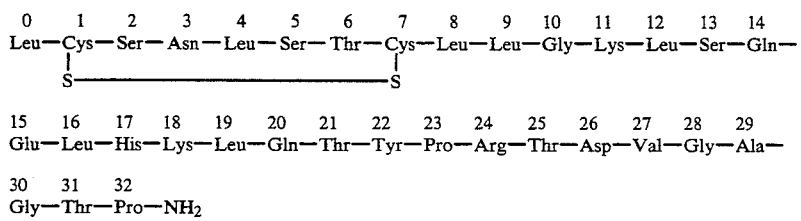

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 13a: [Val⁰, Leu⁸]-eCT; EXAMPLE 13b: [Ile⁰, Leu⁸]-eCT; EXAMPLE 13c: [Met⁰, Leu⁸]-eCT; EXAMPLE 13d: [Thr⁰, Leu⁸]-eCT; EXAMPLE 13e: [Ser⁰, Leu⁸]-eCT; EXAMPLE 13f: [Ala⁰, Leu⁸]-eCT; EXAMPLE 13g: [Norvaline⁰, Leu⁸]-eCT; and EXAMPLE 13h: [Norleucine⁰, Leu⁸]-eCT; were prepared according the above method except for using appropriate amino acid derivatives during the last coupling cycle.

EXAMPLE 13i: [Leu$^{0,8}$, des(19)]-eCT; EXAMPLE 13j: [Leu$^{0,8}$, des(19–22)]-eCT; EXAMPLE 13k: [Val$^0$, Leu$^8$, des(19) ]-eCT; EXAMPLE 13l: [Val$^0$, Leu$^8$, des(19–22) ]-eCT; EXAMPLE 13m: [Ile$^0$, Leu$^8$, des(19)]-eCT; EXAMPLE 13n: [Ile$^0$, Leu$^8$, des(19–22)]-eCT; EXAMPLE 13o: [Met$^0$, Leu$^8$, des(19)]-eCT; EXAMPLE 13p: [Met$^0$, Leu$^8$, des(19–22)]-eCT; EXAMPLE 13q: [Thr$^0$, Leu$^8$, des(19)]-eCT; EXAMPLE 13r: [Thr$^0$, Leu$^8$, des(19–22)]-eCT; EXAMPLE 13s: [Ser$^0$, Leu$^8$, des(19)]-eCT; EXAMPLE 13t: [Ser$^0$, Leu$^8$, des(-19–22)]-eCT; EXAMPLE 13u: [Ala$^0$, Leu$^8$, des(19)]-eCT; EXAMPLE 13v: [Ala$^0$, Leu$^8$, des ( 19–22 )]-eCT;

EXAMPLE 13w: [Norvaline$^0$, Leu$^8$, des(19)]-eCT; EXAMPLE 13x: [Norvaline$^0$, Leu$^8$, des(19–22)]-eCT; EXAMPLE 13y: [Norleucine$^0$, Leu$^8$, des (19) ]-eCT; and EXAMPLE 13z: [Norleucine$^0$, Leu$^8$, des (19–22) ]-eCT were prepared according the above method except for eliminating the coupling cycles for amino acid 19 or 19 through 22 as indicated.

EXAMPLE 14

Synthesis of [Leu$^0$]-eCT

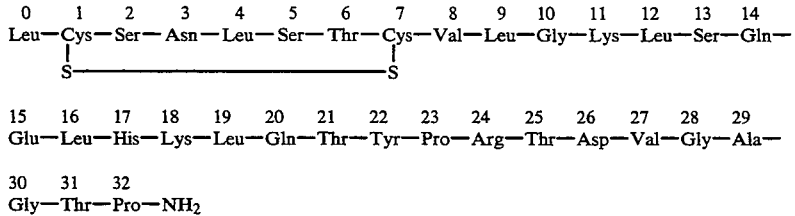

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 14a: [Val$^0$]-eCT; EXAMPLE 14b: [Ile$^0$]-eCT; EXAMPLE 14c: [Met$^0$]-eCT; EXAMPLE 14d: [Thr$^0$]-eCT; EXAMPLE 14e: [Ser$^0$]-eCT; EXAMPLE 14f: [Ala$^0$]-eCT; EXAMPLE 14g: [Norvaline$^0$]-eCT; and EXAMPLE 14h: [Norleucine$^0$]-eCT; were prepared according the above method except for using appropriate amino acid derivatives during the last coupling cycle.

EXAMPLE 15

Synthesis of [Leu$^8$]-sCT

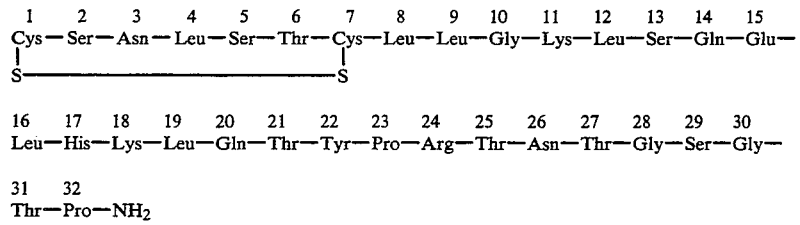

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 16

Synthesis of [Leu$^{0,8}$]-sCT

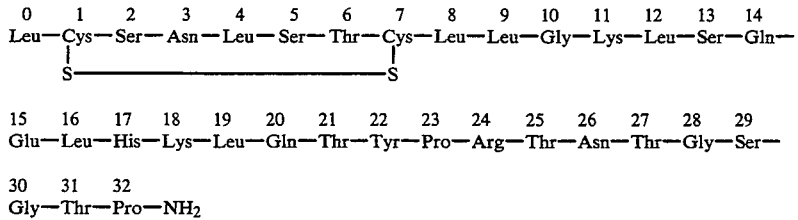

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 16a: [Val$^0$, Leu$^8$]-sCT; EXAMPLE 16b: [Ile$^0$, Leu$^8$]-sCT; EXAMPLE 16c: [Met$^0$, Leu$^8$]-sCT; EXAMPLE 16d: [Thr$^0$, Leu$^8$]-sCT; EXAMPLE 16e: [Ser$^0$, Leu$^8$]-sCT; EXAMPLE 16f: [Ala$^0$, Leu$^8$]-sCT; EXAMPLE 16g: [Norvaline$^0$, Leu$^8$]-sCT; and EXAMPLE 16h: [Norleucine$^0$, Leu$^8$]-sCT; were prepared according the above method except for using appropriate amino acid derivatives during the last coupling cycle.

EXAMPLE 16i: [Leu$^{0,8}$, des(19)]-sCT; EXAMPLE 16j: [Leu$^{0,8}$, des(19–22)]-sCT; EXAMPLE 16k: [Val$^0$, Leu$^8$, des(19)]-sCT; EXAMPLE 16l: [Val$^0$, Leu$^8$, des(-19–22)]-sCT; EXAMPLE 16m: [Ile$^0$, Leu$^8$, des(19)]-sCT; EXAMPLE 16n: [Ile$^0$, Leu$^8$, des(19–22)]-sCT; EXAMPLE 16o: [Met$^0$, Leu$^8$, des(19)]-sCT; EXAMPLE 16p: [Met$^0$, Leu$^8$, des(19–22)]-sCT; EXAMPLE 16q: [Thr$^0$, Leu$^8$, des(19)]-sCT; EXAMPLE 16r: [Thr$^0$, Leu$^8$, des(19–22)]-sCT; EXAMPLE 16s: [Ser$^0$, Leu$^8$, des(19)]-sCT; EXAMPLE 16t: [Ser$^0$, Leu$^8$, des(19–22)]- sCT; EXAMPLE 16u: [Ala⁰, Leu⁸, des(19)]-sCT; EXAMPLE 16v: [Ala⁰, Leu⁸, des(19–22)]-sCT; EXAMPLE 16w: [Norvaline⁰, Leu⁸, des(19)]-sCT; EXAMPLE 16x: [Norvaline⁰, Leu⁸, des(19–22)]-sCT; EXAMPLE 16y: [Norleucine⁰, Leu⁸, des(19)]-sCT; and EXAMPLE 16z: [Norleucine⁰, Leu⁸, des(19)]-sCT were prepared according the above method except for eliminating the coupling cycles for amino acid 19 or 19 through 22 as indicated.

EXAMPLE 17

Synthesis of [Leu⁰]-sCT

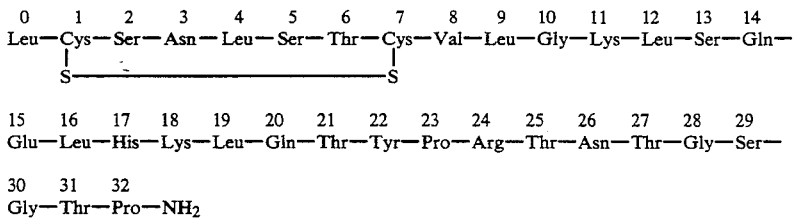

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 17a: [Val⁰]-sCT; EXAMPLE 17b: [Ile⁰]-sCT; EXAMPLE 17c: [Met⁰]-sCT; EXAMPLE 17d: [Thr⁰]-sCT; EXAMPLE 17e: [Ser⁰]-sCT; EXAMPLE 17f: [Ala⁰]-sCT; EXAMPLE 17g: [Norvaline⁰]-sCT; and EXAMPLE 17h: [Norleucine⁰]-sCT; were prepared according the above method except for using appropriate amino acid derivatives during the last coupling cycle.

EXAMPLE 18

Synthesis of [Leu⁸]-rCT

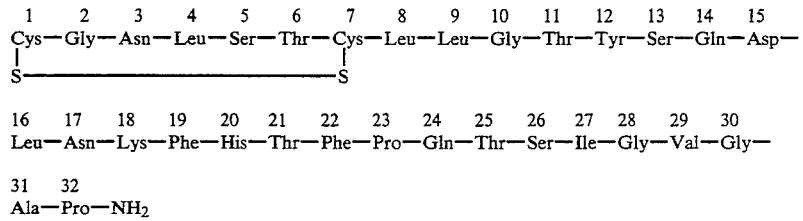

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 19

Synthesis of [Leu⁰,⁸]-rCT

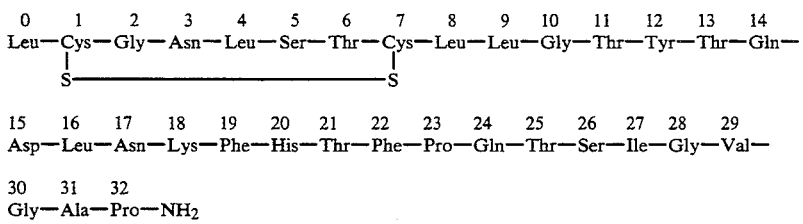

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 19a: [Val⁰, Leu⁸]-rCT; EXAMPLE 19b: [Ile⁰, Leu⁸]-rCT; EXAMPLE 19c: [Met⁰, Leu⁸]-rCT; EXAMPLE 19d: [Thr⁰, Leu⁸]-rCT; EXAMPLE 19e: [Ser⁰, Leu⁸]-rCT; EXAMPLE 19f: [Ala⁰, Leu⁸]-rCT; EXAMPLE 19g: [Norvaline⁰, Leu⁸]-rCT; and EXAMPLE 19h: [Norleucine⁰, Leu⁸]-rCT; were prepared according the above method except for using appropriate amino acid derivatives during the last coupling cycle.

EXAMPLE 20

Synthesis of [Leu⁰]-rCT

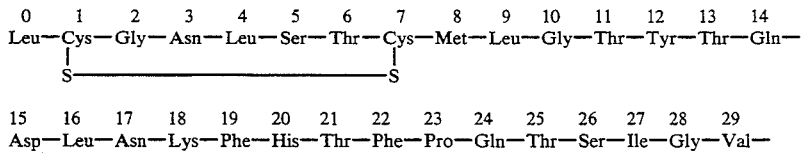

Gly—Ala—Pro—NH₂ (30 31 32)

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 20a: [Val⁰]-rCT; EXAMPLE 20b: [Ile⁰]-rCT; EXAMPLE 20c: [Met⁰]-rCT; EXAMPLE 20d: [Thr⁰]-rCT; EXAMPLE 20e: [Ser⁰]-rCT; EXAMPLE 20f: [Ala⁰]-rCT; EXAMPLE 20g: [Norvaline⁰]-rCT; and EXAMPLE 20h: [Norleucine⁰]-rCT; were prepared according the above method except for using appropriate amino acid derivatives during the last coupling cycle.

purification and characterization was carried out according the procedure described in Example 1.

EXAMPLE 22a: [Val⁰, Leu⁸]-cCT; EXAMPLE 22b: [Ile⁰, Leu⁸]-cCT; EXAMPLE 22c: [Met⁰, Leu⁸]-cCT; EXAMPLE 22d: [Thr⁰, Leu⁸]-cCT; EXAMPLE 22e: [Ser⁰, Leu⁸]-cCT; EXAMPLE 22f: [Ala⁰, Leu⁸]-cCT; EXAMPLE 22g: [Norvaline⁰, Leu⁸]-cCT; and EXAMPLE 22h: [Norleucine⁰, Leu⁸]-cCT; were prepared according the above method except for using appropriate amino acid derivatives during the last coupling cycle.

EXAMPLE 23

Synthesis of [Leu⁰]-cCT

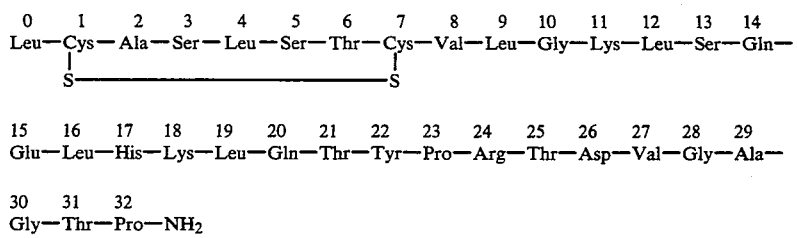

Starting from Boc-Pro-MBHA resin (2 g, 1 mmol), the peptide chain was assembled using appropriate protected amino acid derivatives. Cleavage of the peptide

EXAMPLE 21

Synthesis of [Leu⁸]-cCT

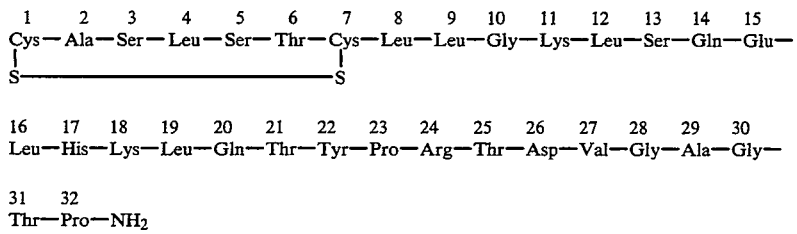

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 22

Synthesis of [Leu⁰,⁸]-cCT

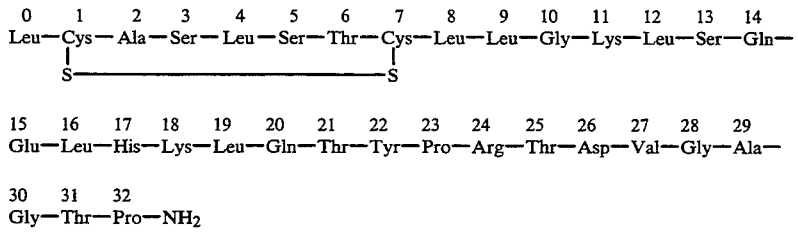

Starting from Boc-Pro-MBHA resin (2 g, 1 mmol), the peptide chain was assembled using appropriate protected amino acid derivatives. Cleavage of the peptide from the resin, formation of the disulfide bridge, and its from the resin, formation of the disulfide bridge, and its purification and characterization was carried out according the procedure described in Example 1.

EXAMPLE 23a: [Val⁰]-cCT; EXAMPLE 23b: [Ile⁰]-cCT; EXAMPLE 23c: [Met⁰]-cCT; EXAMPLE 23d: [Thr⁰]-cCT; EXAMPLE 23e: [Ser⁰]-cCT; EXAMPLE 18f: [Ala⁰]-cCT; EXAMPLE 23g: [Norvaline⁰]-cCT; and EXAMPLE 23h: [Norleucine⁰]-cCT; were prepared according the above method except for using appropriate amino acid derivatives during the last coupling cycle.

EXAMPLE 24

Synthesis of [Leu$^{0,8}$]-pCT

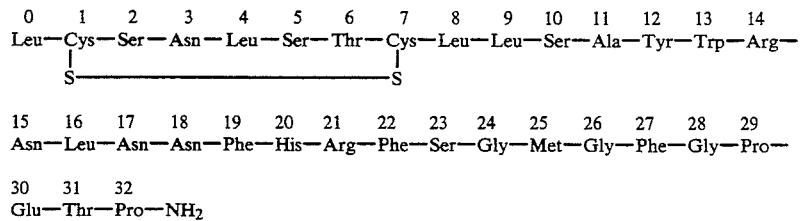

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 24a: [Val$^0$, Leu$^8$]-pCT; EXAMPLE 24b: [Ile$^0$, Leu$^8$]-pCT; EXAMPLE 24c: [Met$^0$, Leu$^8$]-pCT; EXAMPLE 24d: [Thr$^0$, Leu$^8$]-pCT; EXAMPLE 24e: [Ser$^0$, Leu$^8$]-pCT; EXAMPLE 24f: [Ala$^0$, Leu$^8$]-pCT; EXAMPLE 24g: [Norvaline$^0$, Leu$^8$]-pCT; and EXAMPLE 24h: [Norleucine$^0$, Leu$^8$]-pCT; were prepared according the above method except for using appropriate amino acid derivatives during the last coupling cycle.

EXAMPLE 25

Synthesis of [Leu$^8$]-pCT

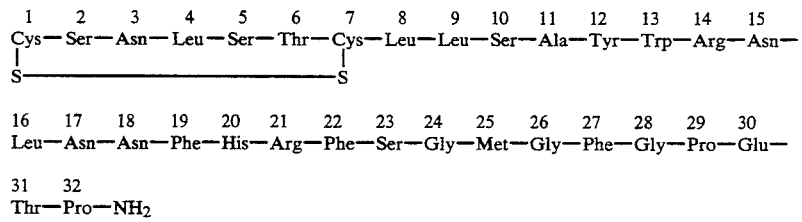

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 26

Synthesis of [Leu$^{0,8}$]-bCT

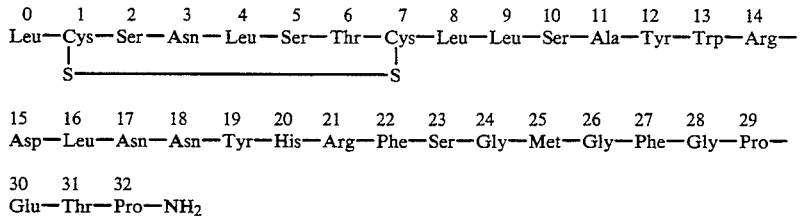

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 26a: [Val$^0$, Leu$^8$]-bCT; EXAMPLE 26b: [Ile$^0$, Leu$^8$]-bCT; EXAMPLE 26c: [Met$^0$, Leu$^8$]-bCT; EXAMPLE 26d: [Thr$^0$, Leu$^8$]-bCT; EXAMPLE 26e: [Ser$^0$, Leu$^8$]-bCT; EXAMPLE 26f: [Ala$^0$, Leu$^8$]-bCT; EXAMPLE 26g: [Norvaline$^0$, Leu$^8$]-bCT; and EXAMPLE 26h: [Norleucine$^0$, Leu$^8$]-bCT; were prepared according the above method except for using appropriate amino acid derivatives during the last coupling cycle.

EXAMPLE 27

Synthesis of [Leu$^8$]-bCT

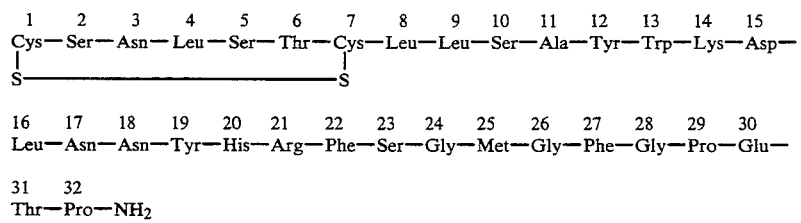

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 28

Synthesis of [Leu$^{0,8}$]-oCT

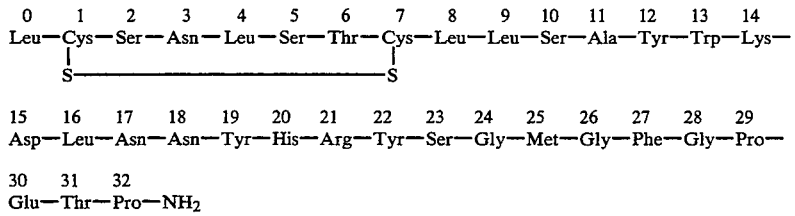

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 28a: [Val$^0$, Leu$^8$]-oCT; EXAMPLE 28b: [Ile$^0$, Leu$^8$]-oCT; EXAMPLE 28c: [Met$^0$, Leu$^8$]-oCT; EXAMPLE 28d: [Thr$^0$, Leu$^8$]-oCT; EXAMPLE 28e: [Ser$^0$, Leu$^8$]-oCT; EXAMPLE 28f: [Ala$^0$, Leu$^8$]-oCT; EXAMPLE 28g: [Norvaline$^0$, Leu$^8$]-oCT; and EXAMPLE 28h: [Norleucine$^0$, Leu$^8$]-oCT; were prepared according the above method except for using appropriate amino acid derivatives during the last coupling cycle.

EXAMPLE 29

Synthesis of [Leu$^8$]-oCT

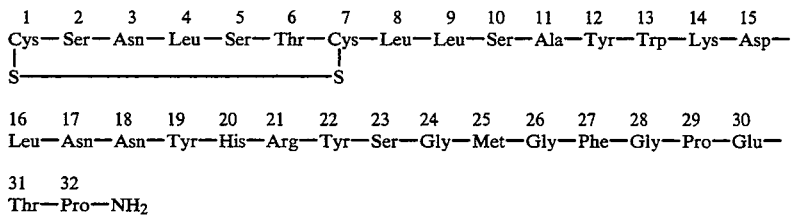

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 1.

EXAMPLE 30

Biological Assay

Peptides of the invention exhibit valuable hypocalcemic activity. This activity is measured as follows: Male rats (Sprague Dawley) weighing approximately 100 grams are fasted overnight. Peptides were dissolved in pH 7.4 PBS buffer at a concentration range of 0.1 microgram to about 100 microgram per ml. The rats were anesthetized with Metofane ®, weighed and injected s.c. with the peptide solutions in a dose of from 0.1 to 100 microgram per KG of body weight. After varying periods of time the animals were anesthetized and an abdominal incision was made; blood samples were taken from the inferior vena cava and the serum was analyzed for calcium by the method of Liedke, *Clinical Chemistry*, 27, 2025–2028 (1981). The amount of peptide necessary for lowering calcium concentration by 10% is defined as 10 IU. According to this method, the hypocalcemic potencies of various calcitonin peptides were determined to be as follows:

| Compound | Hypocalcemic Potency (IU/mg) |
|---|---|
| hCT | 150–200 IU/mg |
| sCT | 4,000 IU/mg |
| cCT | 4,000 IU/mg |
| Example 1: [Leu$^{0,8,12,16}$]-hCT | 4,000 IU/mg |
| Example 2: [Leu$^{0,8,12}$]-hCT | 4,000 IU/mg |
| Example 3: [Leu$^{0,8}$]-hCT | 1,500 IU/mg |
| Example 4: [Leu$^0$]-hCT | 200 IU/mg |
| Example 5: [Leu$^{8,12,16}$]-hCT | 2,000 IU/mg |
| Example 6: [Leu$^{8,12}$]-hCT | 2,000 IU/mg |
| Example 7: [Leu$^8$]-hCT | 500 IU/mg |
| Example 12: [Leu$^8$]-eCT | 5,000 IU/mg |
| Example 13: [Leu$^{0,8}$]-eCT | 6,500 IU/mg |

Example 31

Nasal Bioavailability of Hypocalcemic Peptides

Peptides of the invention, when administered intranasally, show hypocalcemic effects in animals. In order to determine their bioavailability, the effect of hypocalcemic peptides administered intranasally were compared with those administered by intravenous injection, as described below. Nasal powdery formulations containing 100 IU per 30 mg of dry powder were prepared substantially as described in U.S. Pat. No. 4,613,500. Peptides were administered intranasally at a dose of 2.8 IU/kg or intravenously at a dose of 1.75 IU/kg to rabbits. Blood samples were withdrawn before administering the peptides and 0.5, 1, 2, 4, and 6 hours after administration, and serum calcium levels determined. The ratios of areas under the curve of hypocalcemic effect (0 to 6 hours) after nasal and intravenous administration are calculated.

| Compound | Ratio of Nasal: i.v. Bioavailability |
|---|---|
| [Leu$^{8,12,16}$]-hCT | 28.0% |
| [Leu$^8$]-eCT | 28.6% |
| [Leu$^{0,8}$]-eCT | 37.5% |

The invention may be embodied in other specific forms without departing from it in spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

What is claimed is:

1. A hypocalcemic peptide having the formula:

$$Y^0\text{-xCT}$$

wherein Y is a moiety present at position 0, the NH$_2$-terminus of xCT, and is an aliphatic amino acid selected from the group consisting of L- or D-amino acids having a branched or unbranched alkyl side chain of 1 to 8 carbon atoms; L- or D-methionine; L- or D-threonine; L- or D-serine; L- or D-homoserine; and xCT represents the amino acid sequence of human, salmon, eel, rat, bovine, ovine, porcine, rabbit, or chicken calcitonin.

2. A peptide according to claim 1 which is $$(\text{Leu}^0)\text{-xCT}$$

3. A peptide according to claim 2 selected from the group consisting of (Leu$^0$)-hCT; (Leu$^0$)-eCT; (Leu$^0$)-sCT; (Leu$^0$)-cCT; and (Leu$^0$)-rCT, wherein hCT is human calcitonin, eCT is eel calcitonin, sCT is salmon calcitonin, cCT is chicken calcitonin, and rCT is rat calcitonin.

4. A hypocalcemic peptide having the formula:

$$(Y^0)\text{-xCT}$$

wherin Y is selected from the group consisting of aliphatic L-amino acids or D-amino acids having branched or unbranched alkyl side chains of one to eight carbon stoms, L- or D-methionine, L- or D-threonine, L- or D-serine, L- or D-homoserine; and xCT represents the amino acid sequence of human, salmon, eel, rat, bovine, ovine, porcine, or rabbit calcitonin; and optionally having at least one of the amino acid residues at positions 4, 8, 12, 16, 21 and 27 substituted by Y, each Y substituent being independently selected.

5. A peptide according to claim 4 which is $$(\text{Leu}^{0,8})\text{-xCT}.$$

6. A peptide according to claim 5 selected from the group consisting of (Leu$^{0,8}$)-bCT; (Leu$^{0,8}$)-cCT, (Leu$^{0,8}$)-eCT; (Leu$^{0,8}$)-hCT; (Leu$^{0,8}$)-oCT; (Leu$^{0,8}$)-pCT; (Leu$^{0,8}$)-rCT; (Leu$^{0,8}$)-sCT, wherein bCT is bovine calcitonin, cCT is chicken calcitonin, eCT is eel calcitonin; hCT is human calcitonin; oCT is ovine calcitonin, pCT is porcine calcitonin, rCT is rat calcitonin, and sCT is salmon calcitonin.

7. A hypocalcemic peptide having the formula:

$$Y^0\text{-hCT}$$

wherein Y is a Leu moiety present at position 0, the NH$_2$-terminus of xCT, and wherein at least one amino acid residue of hCT is replaced by Y, selected from the group consisting of (Leu$^{0,8,12}$)-hCT; (Leu$^{0,8,12,16}$)-hCT; (Leu$^{0,8,16}$)-hCT; (Leu$^{0,12}$)-hCT; (Leu$^{0,16}$)-hCT or (Leu$^{0,12,16}$)-hCT, wherein hCT represents the amino acid sequence of human calcitonin.

8. A peptide according to claim 4 which is (Leu$^{0,8,12}$)-hCT; (Leu$^{0,8,12,16}$)-hCT; or (Leu$^{0,8,16}$)-hCT, wherein hCT represents the amino acid sequence of human calcitonin.

9. A peptide according to claim 4 wherein the amino acid residues of xCT at positions 4 and 8 are replaced by Y$^4$ and Y$^8$ respectively, and Y$^4$ and Y$^8$ are each an L- or D-amino acid independently selected from the group consisting of Gly, Ala, Leu, Ile, Val, Thr, Nor-Leu, Nor-Val, Met, or Ser.

10. A peptide according to claim 1 wherein Y is an L- or D-amino acid selected from the group consisting of Gly, Ala, Leu, Ile, Val, Thr, Nor-Leu, Nor-Val, Met, or Ser.

11. A peptide according to claim 4 wherein xCT is des (19)-xCT, or des (19–22)-xCT.

12. A peptide according to claim 11 selected from the group consisting of (Leu$^{0,8}$, des(19))-hCT; (Leu$^{0,8}$, des(-19–22))-hCT; (Leu$^{0,8,12}$, des(19))-hCT; (Leu$^{0,8,12}$, des(-19–22))-hCT; (Leu$^{0,8,12,16}$, des(19))-hCT; (Leu$^{0,8,12,16}$, des(19–22))-hCT; (Leu$^{0,8}$, des(19))-eCT; (Leu$^{0,8}$, des(-19–22))-eCT; (Leu$^{0,8}$, des(19))-sCT; (Leu$^{0,8}$, and des(-19–22))-sCT, wherein hCT is human calcitonin, eCT is eel calcitonin, and sCT is salmon calcitonin.

13. A pharmaceutical composition comprising an effective blood calcium-reducing amount of a peptide having the structure set forth in claims 1, 11 or 4 in combination with a pharmaceutically acceptable carrier.

14. A method of treating disease by reducing serum calcium levels in a mammal, comprising to said mammal in need of such treatment an effective, blood calcium-reducing amount of a calcitonin peptide analogue having the structure set forth in any one of claims 1, 11 or 4.

15. A method of treating Paget's disease or osteoporosis, comprising:

administering to an affected subject a bone resorption-opposing amount of a synthetic calcitonin having the structure set forth in any one of claims 1, 11 or 4 whereby the resorption of bone associated with said diseases is reduced or eliminated.

16. A method of treating bone pain, comprising:

administering a effective pain-relieving amount of a synthetic calcitonin having the structure set forth in any one of claims 1, 11 or 5 to a subject in need thereof, whereby the bone pain associated with osteoporosis, osteoporotic fractures, Paget's disease, or osteolysis of malignancy is reduced or eliminated.

* * * * *

UNITED STATES PATENT AND TRADEMARK OFFICE
CERTIFICATE OF CORRECTION

PATENT NO. : 5,364,840
DATED : November 15, 1994
INVENTOR(S) : Basava et al

It is certified that error appears in the above-indentified patent and that said Letters Patent is hereby corrected as shown below:

Column 29, line 39, change "carbon stoms, L- or" to --carbon atoms L-or--.
Column 30, line 56, change "claims 1, 11 or 5" to --claims 1, 11, or 4--.

Signed and Sealed this

Thirtieth Day of May, 1995

Attest:

BRUCE LEHMAN

Attesting Officer

Commissioner of Patents and Trademarks